United States Patent [19]

Stroetmann et al.

[11] Patent Number: 5,578,061
[45] Date of Patent: Nov. 26, 1996

[54] METHOD AND APPARATUS FOR CARDIAC THERAPY BY STIMULATION OF A PHYSIOLOGICAL REPRESENTATIVE OF THE PARASYMPATHETIC NERVOUS SYSTEM

[75] Inventors: Brigitte Stroetmann, Uttenreuth, Germany; Nils Holmström, Järfälla, Sweden; Siegfried Kallert, Erlangen, Germany; Staffan Bowald, Almunge, Sweden

[73] Assignee: Pacesetter AB, Solna, Sweden

[21] Appl. No.: 538,570

[22] Filed: Oct. 3, 1995

[51] Int. Cl.⁶ .................................................. A61N 1/362
[52] U.S. Cl. ........................................... 607/4; 607/5
[58] Field of Search ................................. 607/4, 5, 7, 9, 607/11, 14

[56] References Cited

U.S. PATENT DOCUMENTS

| | | | |
|---|---|---|---|
| 3,421,511 | 1/1969 | Schwartz | 607/48 |
| 3,522,811 | 8/1970 | Schwartz | 607/48 |
| 3,650,277 | 3/1972 | Sjostrand et al. | 607/48 |
| 5,199,428 | 4/1993 | Obel et al. | 128/703 |
| 5,203,326 | 4/1993 | Collins | 607/4 |
| 5,215,086 | 6/1993 | Terry et al. | 607/118 |
| 5,318,592 | 6/1994 | Schaldach | 607/5 |
| 5,330,507 | 7/1994 | Schwartz | 607/14 |
| 5,366,484 | 11/1994 | Kroll | 607/5 |

FOREIGN PATENT DOCUMENTS 0588127  3/1994  European Pat. Off. .................. 607/5

Primary Examiner—William E. Kamm
Assistant Examiner—George R. Evanisko
Attorney, Agent, or Firm—Hill, Steadman & Simpson

[57] ABSTRACT

A device for heart therapy has a tacharrythmia detector unit, a control unit and a current generator. The current generator controlled by the control unit emits via an electrode system a first, pulsed current to a physiological representative of the parasympathetic nervous system in order to activate same in response to detection of an impending or established arrhythmia. The current generator is further caused by the control unit, in the event of tachyarrythmia detection to emit, via the electrode system, a second current to a physiological representative of the sympathetic nervous system in order to block same.

27 Claims, 4 Drawing Sheets

5,578,061

METHOD AND APPARATUS FOR CARDIAC THERAPY BY STIMULATION OF A PHYSIOLOGICAL REPRESENTATIVE OF THE PARASYMPATHETIC NERVOUS SYSTEM

BACKGROUND OF THE INVENTION

1. Field of the Invention

The present invention is directed to a method and apparatus for heart therapy of the type wherein a pulsed stimulation current is supplied to a physiological representative of the parasympathetic nerve in order to activate same in response to a detection of an impending (incipient) or established arrhythmia.

2. Description of the Prior Art

A modern, automatic, implantable defibrillator, e.g. as described in Current Problems in Cardiology, Volume XIV, No. 12, Dec. 1989, Chicago, Troup J. P. "Implantable Cardioverters and Defibrillators", pp. 699–700, includes cardioversion and pacemaker stimulation options, for both tachycardia and bradycardia in addition to the defibrillation function and is sometimes referred to as an AICD (automatic implantable cardioverter defibrillator). In AICD defibrillation, an attempt is made to induce all heart cells to depolarize simultaneously by applying a strong electrical field across the heart, i.e. The heart is given an electrical shock. The electrical shock is in the form of electrical pulses which can sometimes be delivered in more or less sophisticated spatial and chronological patterns.

Considerable electrical energy (5–40 J) is required for defibrillation, and thus tissue subjected to the shock could be damaged. For this and other reasons, attempts are being made to reduce the electrical energy needed for defibrillation. Within the scope of the ACID prior art, a radical reduction in energy, i.e. a reduction on the order of a factor of ten or more, is actually only possible, in the event of an arrhythmia such as tachycardia, which sometimes appears prior to a fibrillation episode, when the therapeutic device operates with ATP (anti-tachycardia pacing). With ATP, pacing pulses are emitted in relation to the tachycardia beats in a pattern causing the pacing pulses to terminate the tachycardia. There, the energy of the pacing pulses in ATP is of the same magnitude as for conventional pacing pulses for bradycardia, i.e. on the order of microjoules. The ATP technique, however, is only applicable to a tachycardia which may precede the fibrillation episode, and cannot replace defibrillation of a heart exhibiting established ventricular fibrillation.

In therapy in the form of electrical nerve stimulation for treating disorders others than those occurring in the heart in tachyarrhythmias, it has long been known that the energy required is very small, as in pacemaker treatment of the heart, compared to the above-described conventional levels in defibrillation.

Electrical nerve stimulation and the energy needed therefor can be achieved with a modern system for stimulation of the vagus nerve in the treatment of epilepsy, as described in an article by Tarver et al.: "Clinical Experience with Helical Bipolar Stimulating Lead", Pace, Vol. 15, October, Part II 1992, This system employs a pulse generator which is subcutaneously implanted in the upper left part of the thorax region and which is connected to a nerve-stimulating electrode arranged around the left vagus nerve in the nec area. During nerve stimulation, the generator emits 0–12 mA pulses with a pulse width of 130 to 1000 microseconds.

A heart therapy device based on electrical nerve stimulation may thus be one way of addressing the problem of the high levels of energy needed in conventional AICD techniques. The heart's innervation will now be briefly described in order to provide an explanation of the way such a heart therapy device could be achieved.

The vagus nerve is also of interest as regards the heart and the action of the nervous system thereon, since this nerve forms a part of the autonomic nerve system. The autonomic nerve system innervates the heart in the form of two subsystem, the sympathetic and the parasympathetic. From the physiological point of view, these systems are represented by a number of nerves or nerve strings (with attendant ganglia) in different locations. The terms "sympathetic nerve", and "vagus nerve" will often be used below, for simplicity, for the two sub-systems and attendant nerves/nerve strings, despite the actual complexity of innervation. Details will, however, be provided in the description when needed for the understanding. Increased signal activity in the sympathetic nerve increases heart activity (heart rate and stroke volume), whereas increased signal activity in the vagus nerve reduces heart activity (heart rate). Activity in the sympathetic nerve and the vagus nerve normally balance each other so that the heart maintains an appropriate rate at rest of about 70 beats/minute.

Partly in view of the above considerations, activating electrical stimulation of the vagus nerve for prophylaxis and treatment of both ventricular and supraventricular arrhythmias has recently been proposed (Max Schaldach "Electrotherapy of the heart", 1992, Springer Verlag Heidelberg, pp. 210–214). As described therein, the increased activity in the sympathetic nerve in the case of impending or established tachyarrythmia is monitored by intraventricular measurement of impedance, i.e. by indirect measurement of sympathetic activity, in order to control the emission of activating electrical pulses to the vagus nerve during impending or established tachyarrythmia.

The present inventors, in their own animal experiments and measurements concerning tachyarrhythmias encompassing fibrillation, were unable to find any defibrillation effect arising from stimulation of the vagus nerve during established, ventricular fibrillation.

SUMMARY OF THE INVENTION

An object of the present invention is to achieve an effective heart therapy device and method with low energy requirements prophylactic and acute treatment of tacharrythmia by nerve stimulation, for defibrillation in particular.

The above object is achieve in accordance with the principles of the present invention in a method and an apparatus wherein, following the detection of an impending or established arrhythmia, a first pulses current is supplied to a physiological representative of the parasympathetic nervous system in order to activate the parasympathetic nervous system, and a second current is also supplied via an electrode system to a physiological representative of the sympathetic nervous system in order to block the sympathetic nervous system with respect to its action on the heart.

The invention is described in greater detail with reference to an embodiment as disclosed in the attached drawings of a device according to the invention for heart therapy as applied in the above-described AICD defibrillator system. For illustative—not restrictive—reasons, the device according to the invention will henceforth be designated in this description as a "a nerve-stimulating heart defibrillator" or a "nerve-heat defibrillator" whose task is to terminate fibrillation in the heart. It is to be understood that also other tachyarrhythmias, such as impending but as yet unestablished fibrillation treated with ATP or cardioversion according to conventional techniques, can be treated and that the designation "nerve-heart defibrillator" in this context is a term only employed for explanatory purposes. Although the nerve-heart stimulator is explained and described herein in conjunction with a AICD-type defibrillator system, it is further understood that the nerve-heart stimulator can be employed independently without all the parts in the described defibrillator system.

DESCRIPTION OF THE PREFERRED EMBODIMENTS

Figure 1:
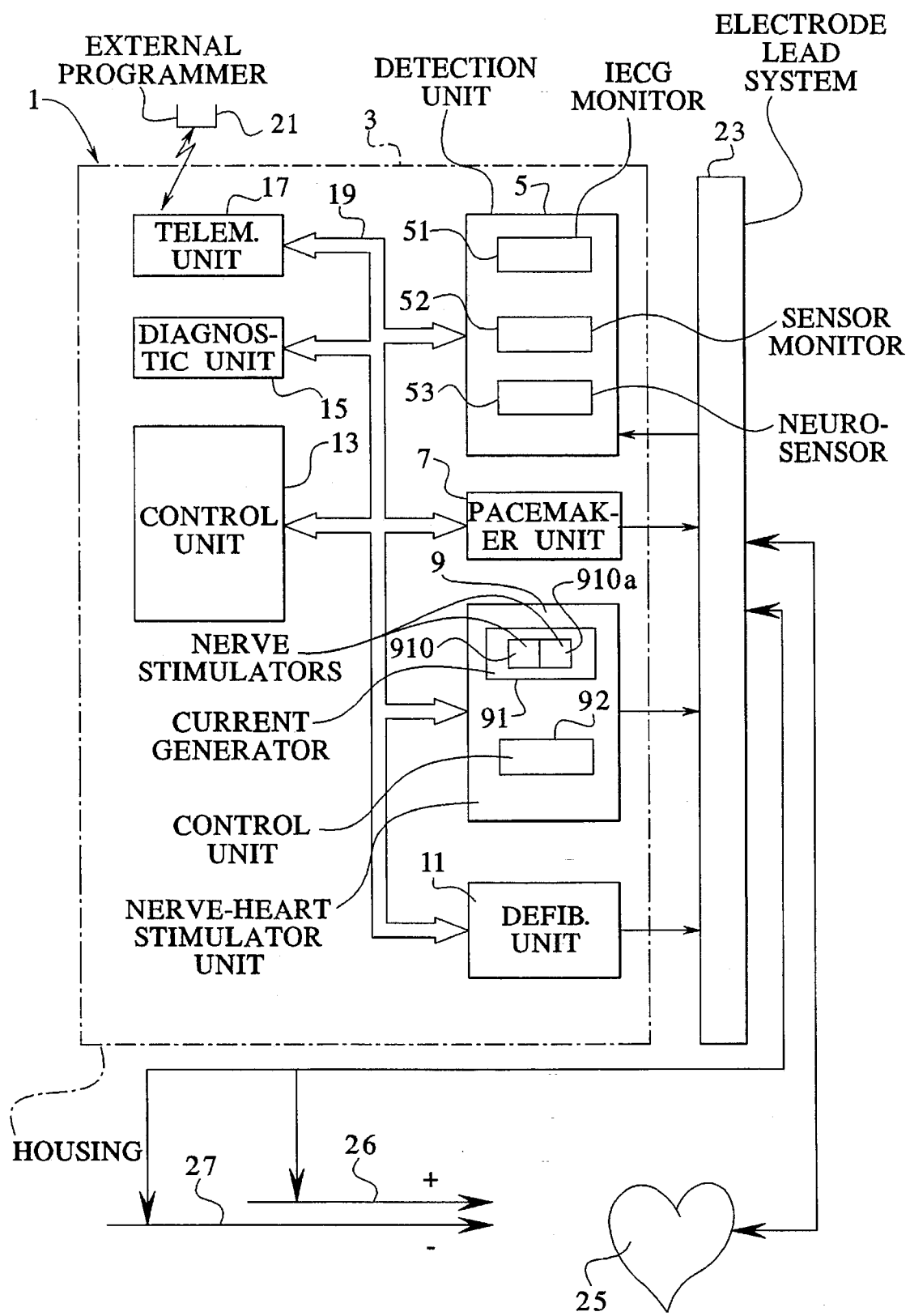
FIG. 1 is a block diagram of a defibrillator system, embodying a nerve-heart defibrillator according to the invention.

FIG. 1 shows an example of a defibrillation system using the nerve-heart defibrillator according to the invention, in which defibrillator implant is generally referenced 1. The implant 1 has an enclosure which may consist of e.g. a titanium capsule 3. The implant 1 includes a detection unit 5, a pacemaker unit 7, which can emit stimulation pulses to the heart both in the case of bradycardia and in the case of tachycardia, a nerve-heart defibrillation unit 9, an electrical defibrillation unit 11, a control unit 13, a diagnosis unit 15 and a telemetry unit 17. The different units in the implant 1 communicate internally via a data bus 19.

The implant 1 communicates with an external programmer 21 via the telemetry unit 17, whereby communications primarily include the transmission of programming data to the implant 1 and transmission of diagnostic data, e.g. about different events in the heart, sensor signals and ECG signals, from the diagnostic unit 15.

The implant 1 is connected to a heart 25 via an electrode lead system 23 of attendant conventional electrodes for emitting pacing as well as defibrillation pulses (including pulses with somewhat less energy then the level required for defibrillation, e.g. cardioversion pulses) to the heart 25 and for picking of signals indicative of the heart's condition. It should be noted that FIG. 1 is only schematic, and the signals designating the heart's condition also encompass sensor signals obtained from the sensing of heart-related physiological variables elsewhere in the body, e.g. hemodynamics (pressure/flow) in the vascular system. A blood pressure-sensing body could, e.g., be arranged in the patient's neck area around a blood vessel (neck artery or vein), whereby the sensing body may consist of a ring-shaped (possibly suturable) holder device and a sensing device on the inside of the holder device in the form of a pressure-sensitive cuff.

The implant 1 is also in connection via the electrode (connection ?) system 23 with the sympathetic nerve 26 (a plus sign designates an activating effect on heart activity) and the vagus nerve 27 (a minus sign designates an inhibitory effect on heart activity) via the system 23 of electrodes and electrode leads in order to emit nerve-stimulating pulses to the vague nerve 27 and blocking current to the sympathetic nerve 26 and for picking up heart-related nerve signals therefrom. An embodiment showing details of the nerve electrodes is shown in FIG. 4, described in more detail below.

The defibrillator implant 1 accordingly includes, in addition to the nerve-heart defibrillator unit 9 described below, circuitry for performing the functions found in a modern defibrillator (AICD) of the type noted above. Thus, the heart's condition is monitored in the detection unit 5 by means of an IECG-monitoring device 51 and a sensor signal-monitoring device 52 (for e.g. hemodynamics). Heart-related nerve signals are also monitored in the detection unit 5 in a nerve signal-monitoring device or neurosensor 53. Such a sensor 53 may be formed by a comparator with a threshold value defining a condition for the presence of an arrhythmia. If sensed nervous activity meets the condition, the comparator issues an arrhythmia-indicating output signal. Thus normal sinus rhythm and abnormal conditions in the heart, the later possibly being bradycardia, hemodynamically unstable tachycardia and ventricular fibrillation requiring treatment, as well as nerve (sympathetic) signal activity indicating that the above conditions are established or impending, are detected in the detection unit 5.

Data from the detection unit 5 are sent to the control unit 13 which, depending on the data, orders a requisite therapy, such as tachycardia-terminating heart stimulation, and also sends a command signal to at least one of the units 7, 9 and 11. In the case of a determination that tachycardia-terminating stimulation is need, the command signal is sent to the pacemaker unit 7.

Except for the nerve-heart defibrillator unit 9 and parts of the detection unit 5 (the neurosensor 53 in particular), the above-described components and functions are conventional in nature, as noted above. They will henceforth thus only be considered to the extent they relate to the nerve-heart stimulator unit 9, which will now be described, and the neurosensor 53, to be described subsequently, in the following description.

The nerve-heart stimulator unit includes a current generator 91 for nerve stimulation and is capable of supply nerve-activating pulsed current with a balanced average current level, e.g. with a frequency range of 20 to 50 Hz, a pulse amplitude of 0–9 V and a pulse width of 0.1–1 me, from a nerve stimulator 910, in addition to nerve-blocking direct current/high-frequency current, to be discussed subsequently. The unit 9 further includes a time control unit 92 which is capable of supplying control information to the current generator 91 regarding e.g., which activating and blocking pulses, pulse sequences and continuous output signals should be delivered via the electrode system 23 from the unit 9 to the sympathetic nerve 26 and vagus nerve 27, respectively, and also when the pulses are to be emitted. It should also be noted that the pulses supplied from the unit 9 may additionally include other suitable forms of pulses, such as dual biphasic pulses and alternatingly biphasic pulses separated by a pulses interval. The operating parameters of the current generator 91 and of the time control unit 92 are, like other parameters in the implant 1, programmable via the telemetry unit 17. Therapy supplied from the unit 9 can be supplied, repeatedly if need be, over a period of time, e.g. 5 to 10 seconds, suitable to the therapy. The time control unit 92 is shown, merely for illustrative purposes, as a separate unit in the unit 9. It can naturally be an integrated part of the current generator 91.

Figure 2A:
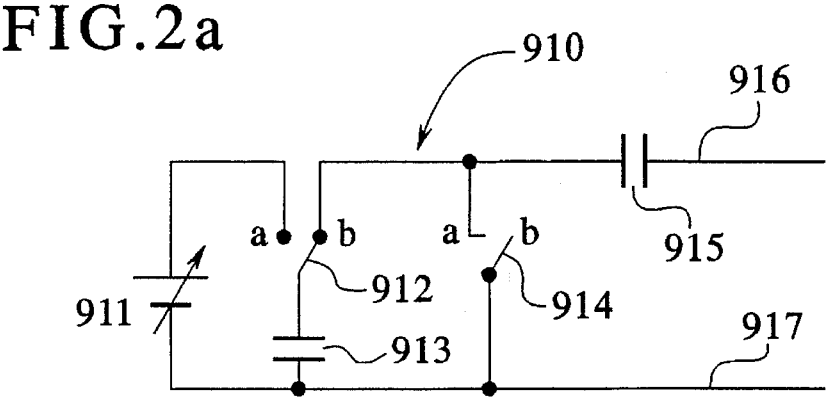
FIGS. 2a and 2b respectively show examples of a vagus nerve stimulator in the nerve-heart defibrillator.

FIG. 2a shows an example of the nerve stimulator 910, which emits pulsed current for activating nerve stimulation, in the current generator 91. A voltage source 911 with a variable voltage V is connectable, via a switch 912, to a capacitor 913 with capacitance C. The capacitor 913 is also connectable, via the switch 912, to a capacitor 915, also with capacitance C. The capacitor 915 is connectable, via a switch 914, to an electrode output terminal 917. The nerve stimulator 910 can assume two states, a first state when the two switches 912 and 914 (both of which are controlled in parallel by the time control unit 92) assume the position designated a FIG. 2a, and a second state when the two switches 912 and 914 assume the position designated b. In the second state, the capacitors 913 and 915 are connected in series, whereupon the capacitor 913, which is charged to voltage V from the voltage source 911, is discharged via the capacitor 915 and the electrode output terminals 916 and 917. In the first state, the capacitor 913 is connected to the voltage source 911 by the switch 912, whereupon the capacitor 915 is also discharged via the electrode output terminals 916 and 917 and the patient. Control of events is exercised by the time control unit 92. The capacitance C for the capacitors 913 and 915 may, e.g., be 100 µF.

Figure 2B:
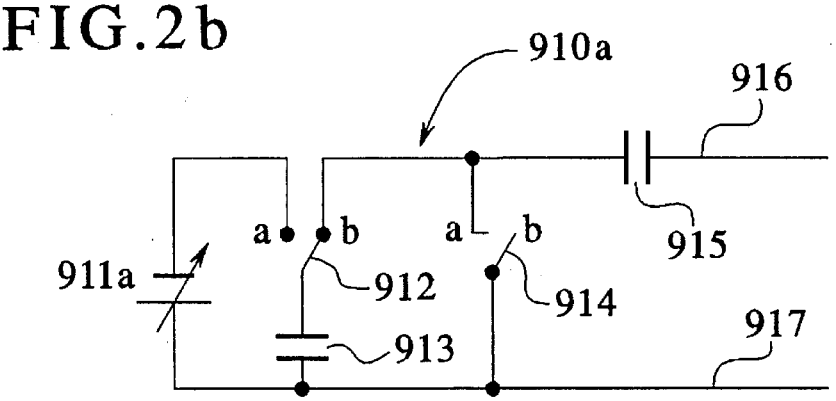
Figure 3:
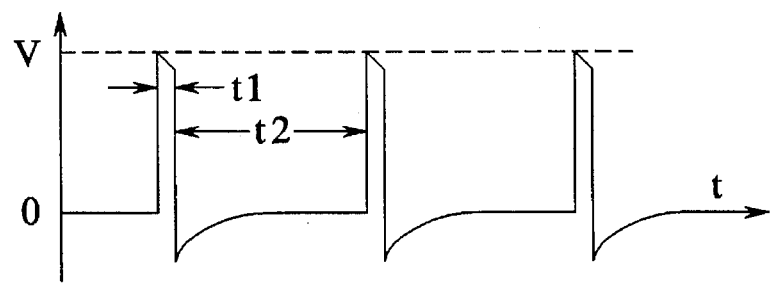
FIG. 3 shows illustrative examples of patterns of vagus nerve stimulation pulses generated in accordance with the invention.

Examples of pulses emitted by the unit 9 are shown in FIG. 3. FIG. 3 shows the output signal over time t between the electrode output terminals 916 and 917 in FIG. 2. The pulse width t1 may be 0.5 ms, and the pulse interval t2 may be 50 ms (20 Hz) in moderate stimulation. In maximum stimulation, t2 is reduced to about 20 ms (50 Hz). The amplitude of the output voltage V is not affected as long as the output voltage V is above a threshold for stimulation of all fibers in the nerve. The threshold is electrode-related and amounts to about 5 volts for the electrode used here and described below.

An electrode (to be described below for the vagus nerve in conjunction with FIG. 4) in the system 23 and electrode cable for the respective nerve to be stimulated can consist of one or more flexible electrical conductors made of, e.g., MP35, each conductor being enclosed in electrical insulation made of, e.g., silicone rubber. The collective silicone rubber insulation on the conductors serves as the electrode cable's outer sheath. The electrode is devised for bipolar stimulation and has a first sub-electrode for the cathode and a second sub-electrode for the anode.

The sub-electrodes can be devised as cuffs, rings, helices or the like with e.g. platinum, and other electrically conducting metals and/or polymers, as well as carbon fibers/meshes as electrode material in contact with the nerve and an electrically insulating and mechanically resilient sheath of silicone rubber around the electrode material. The silicone rubber is pre-tensioned to some degree so that electrode, after implantation, retains mechanical and electrical contact with the nerve. The electrode can also be provided with suturing appliances and a device for mechanically relieving the load on the sub-electrodes, e.g. silicone rubber anchoring around the nerve with tensile relief for the conductors of the sub-electrodes. The electrode may also be anchored, with a constructively adapted design, in a blood vessel, preferably a venous vessel, immediately adjacent to the nerve.

A construction which is similar in all essential respects to the construction described for the stimulation electrodes can also be used for the sensor electrode employed for sensing heart-related activity in the sympathetic nerve. The vagus nerve could also be used, but the description relates to the sympathetic nerve as an example, whereby the nerve signals are sent to the nerve signal monitoring device 53 in the detection unit 5. The sensor electrode for the sympathetic nerve 26 can simultaneously serve as the stimulation electrode for the sympathetic nerve 26.

Figure 4A:
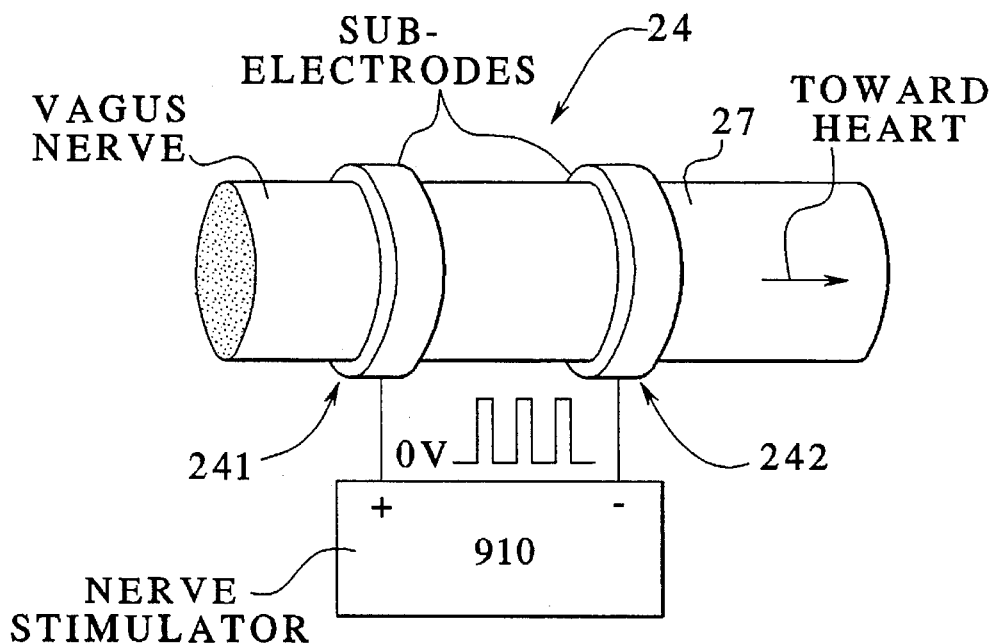
FIGS. 4a, 4b, 4c and 4d respectively show examples of the structure of a nerve electrode suitable for use in accordance with the invention.

FIG. 4a shows an example of the construction principles for a cylindrical nerve electrode used herein and applicable to a nerve. FIG. 4a shows the vagus nerve 27 and an electrode 24, consisting of a sub-electrode 241 arranged distal to the heart and a sub-electrode 242 arranged proximal to the heart 25, arranged thereon. The arrow in FIG. 4 points toward the heart 25. The sub-electrodes 241 and 242 are for activating stimulation and are connected via conductors in the system 23 (FIG. 1) to the plus output terminal 916 and the minus output terminal 917, respectively, of the nerve stimulator 910. If the sub electrode 241 lead to an anodic block the result is that the main direction of nerve impulses is toward the heart 25.

Figure 4B:
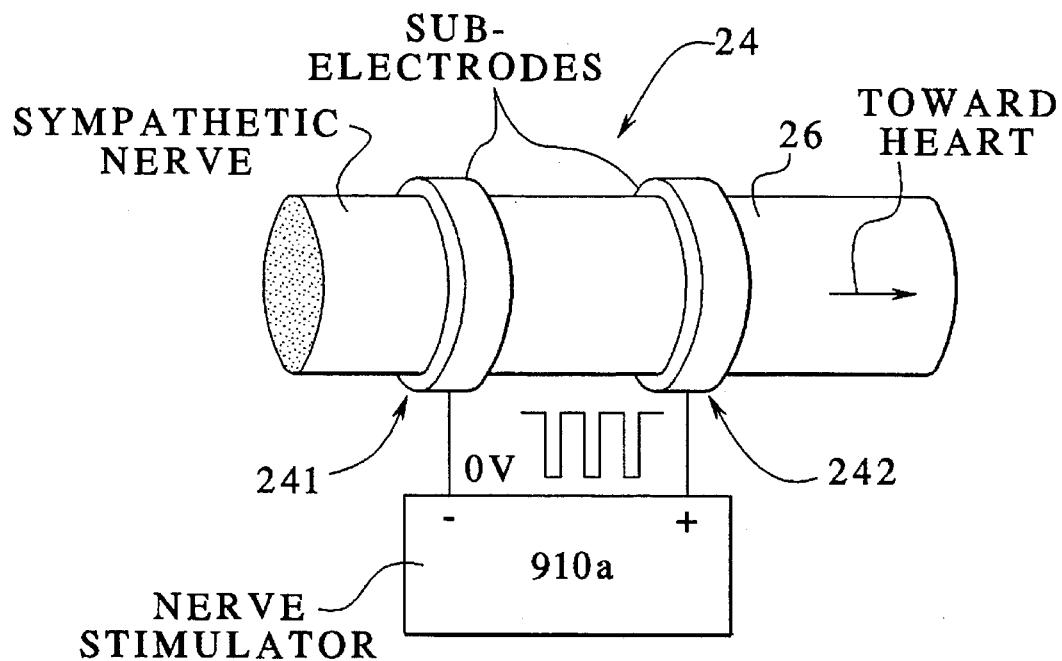
Figure 4C:
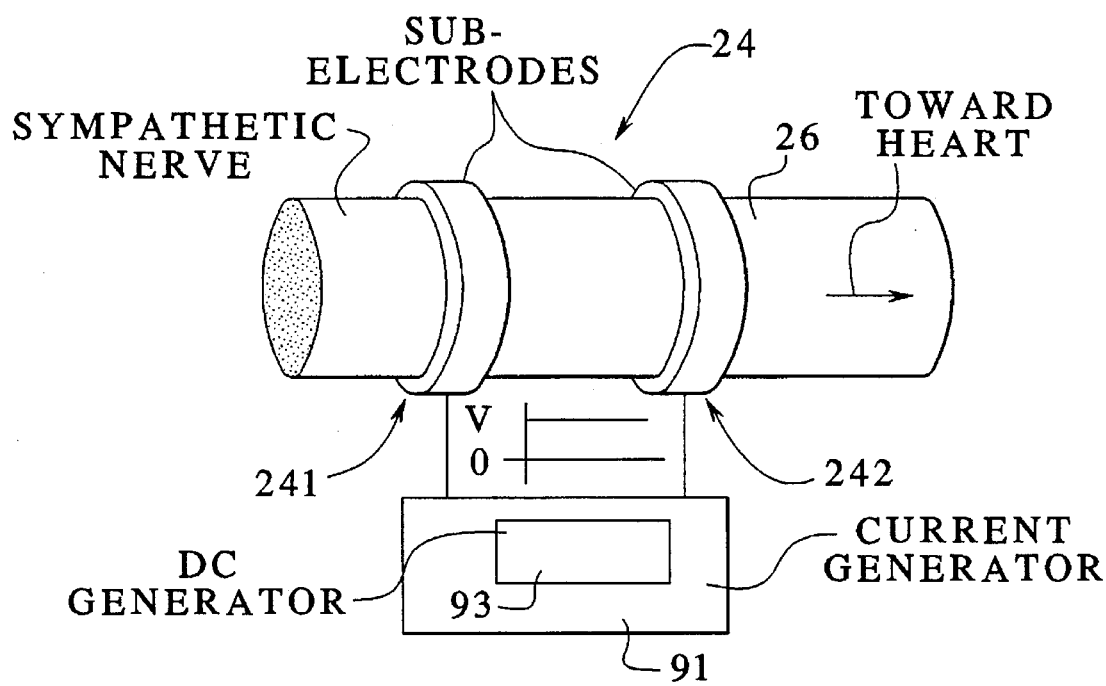
Figure 4D:
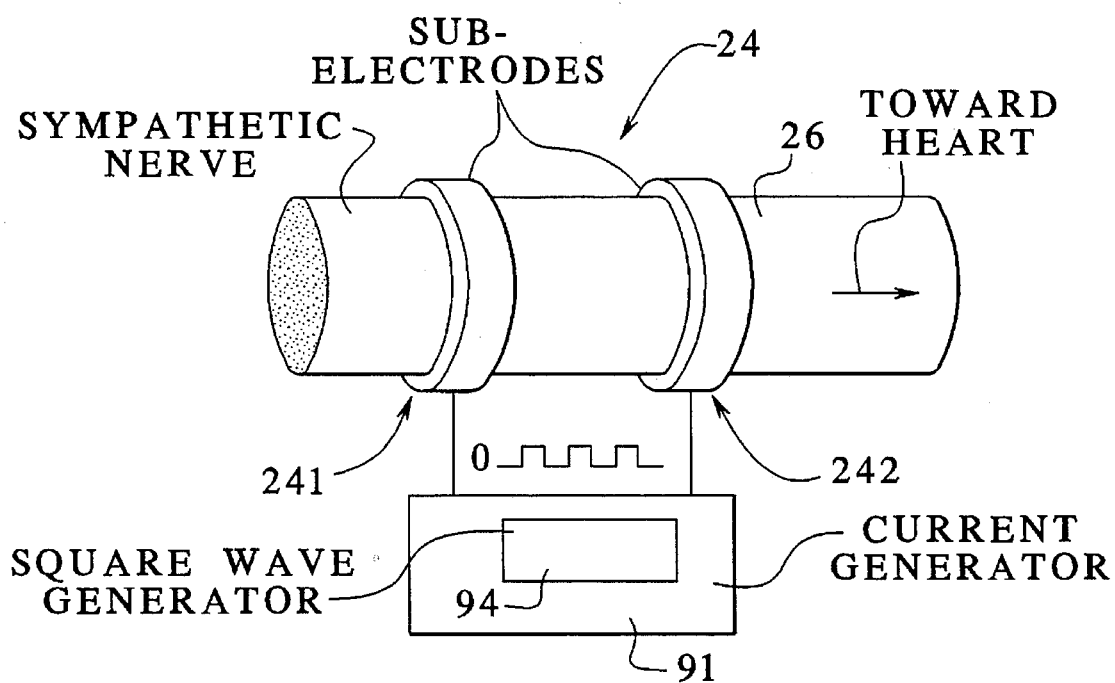

As previously noted, the current generator 91 can also emit a current for blocking the sympathetic nerve 26, in addition to emitting the described pulses from the nerve stimulator 910 for activating the vagus nerve 27. One such blocking current can be achieved by additionally arranging, in the current generator 91, a pole-reversed nerve stimulator 910a, shown in FIG. 2b with reversed-polarity voltage source 911s, which emits pulses, as shown in FIG. 3, but with the opposite polarity the sub-electrode 242 becomes positive and so the sub-electrode 241 negative, as shown in FIG. 4b. Here, the frequency of the emitted blocking pulses should range from 200 to 500 Hz so the action potential in the nerve never has time to drop. Another way to achieve a nerve blockage is to provide the current generator 91 with a direct current generator 93 as shown in FIG. 4c for emitting a direct current which can be applied to the sympathetic nerve 26 as a direct current from the plus pole of the direct current generator for e.g. a few seconds. Instead of a direct current a square wave provided by a square wave generator 94 can be employed as shown in FIG. 4d.

Stimulation and any sensor electrodes for the sympathetic nerve and the vagus nerve are preferably implanted in the patient's neck area. For the vagus nerve 27, the preferred implantation site is in the neck area by or near the right middle portion of the external carotid artery. For the sympathetic nerve, the preferred implantation site, as regards stimulation, is the ganglion stellatum, whereby an electrode adapted to used with this thickened part of the nerve is employed.

The nerve-heart defibrillator described herein and including the unit 9 therefore achieves defibrillation of the heart 25 by delivering an activating current to the vagus nerve 27 and a blocking current to the sympathetic nerve 26 from the block 9 in response to one or more fibrillation conditions detected by the units 51, 52 and 53 in the detection unit 5. If the fibrillation persists, despite this treatment (which can be repeated if necessary) from the nerve-heart defibrillator unit 9, the control unit 13 can order collaboration with other parts of the defibrillator implant 1 which are relevant to the persistent fibrillation condition, so that one or more electrical defibrillation shocks are emitted by the block 11 for electrical defibrillation.

It should be noted that the nerve-heart stimulator unit 9 according to the invention in the defibrillator implant 1 is also capable of treating, as previously noted, impending but as yet unestablished fibrillation conditions (or other refractory tachyarrythmia) by prophylactically applying an activating current to the vagus nerve 27 and a blocking current to the sympathetic nerve 26, as described above.

The nerve signal monitoring device 53 contributes to improved monitoring by the detection unit 5 as regards tachyarrhythmias. The device 53 is, e.g., arranged to be able to observe changes in the signal patterns of the autonomic nervous system generated by e.g. myocardial ischemia, a condition which often precedes a tachyarrythmia. When the signal patterns are registered with an electrode as described herein (FIG. 4) and these patterns are processed (e.g. compared to patterns which are present under normal conditions), changes can be detected in sufficient time before dangerous tachyarrythmia becomes established.

One example of the course in treatment with the nerve-heart defibrillator unit 9, utilizing the neurosensor 53 and collaborating with other units in the defibrillator implant 1, is provided below.

As soon as the detector unit 5 detects impending fibrillation or some other dangerous, impending tachyrhythmia (e.g. a change in the activity of the autonomic nervous system), treatment from the unit 9 can be started in the form of light activation of the vagus nerve 27 for 5 seconds. If the detector unit 5 detects a return to a normal state of the heart 25, treatment is terminated. If the detector unit 5 continues to detect an abnormal condition for the heart 25, treatment will continue, supplemented with blocking of the sympathetic nerve, preferably at the ganglion stellatum, for a few seconds. If heart activity drops below a given rate because of the current delivered to the vagus nerve and the sympathetic nerve, the pacemaker block 7 automatically begins stimulating the heart 25 in order to maintain or restore its sinus rhythm. Treatment is terminated if the detector 5 now shows that the heart 25 has returned to a normal state. If this is not the case, the electrical defibrillator block 11 can be activated in order to shock the heart 25 in the conventional way.

Although the nerve-heart stimulator unit 9 has been described in the context of a conventional implant which also comprises many other units, the described example clearly only shows some of the therapy possibilities of the nerve-heart defibrillator 9 and shall not be interpreted as any restriction on its use. The nerve-heat stimulator unit 9 can alternatively, in treatment of supraventricular arrhythmias, only include the parts which stimulate the vagus nerve. In the treatment of supraventricular arrhythmias, the nerve-heart stimulator does not necessary have to be implanted in the patient's body. It can also be used extracorporeally, e.g. for temporary use with appropriately situated external and internal nerve electrodes.

Although modifications and changes may be suggested by those skilled in the art, it is the intention of the inventors to embody within the patent warranted hereon all changes and modifications as reasonably and properly como within the scope of their contribution to the art.

We claim as our invention:

1. An apparatus for providing therapy to the heart of a subject, comprising:

a tachyarrhythmia detector means for detecting tachyarrhythmia of said heart;

a current generator;

an electrode system means connectable for delivering current from said current generator in vivo to the parasympathetic nervous system of said subject and for delivering current from said current generator in vivo to the sympathetic nervous system of said subject; and control means for causing said current generator, upon detection of tachyarrhythmia by said tachyarrhythmia detector, to emit a first, pulsed current via said electrode system to the parasympathetic nervous system in order to activate said parasympathetic nervous system and to emit a second current via said electrode system to the sympathetic nervous system for blocking said sympathetic nervous system.

2. An apparatus as claimed in claim 1 wherein said current generator includes a first nerve stimulator from which said first, pulsed current is emitted, and wherein said control means comprises means for causing said first nerve stimulator to emit pulses each having a pulse width in a range of 0.1–1.0 ms in a sequence with a pulse interval in a range from 20–50 ms.

3. An apparatus as claimed in claim 2 wherein said control means comprises means for causing said first stimulator to emit said pulses with a pulse width of 0.5 ms.

4. An apparatus as claimed in claim 2 wherein said current generator includes a second nerve stimulator which emits said second current, said second nerve stimulator having opposite polarity with respect to said first nerve stimulator, and said control means comprises means for causing said second nerve stimulator to emit said second current in the form of pulses each having a pulse width in a range from 0.1–1.0 ms in a sequence with a pulse interval in a range from 2–5 ms.

5. An apparatus as claimed in claim 4 wherein said control means comprises means for causing said second nerve stimulator to emit said pulses with a pulse width of 0.5 ms.

6. An apparatus as claimed in claim 1 wherein said current generator comprises means for emitting said second current as direct current.

7. An apparatus as claimed in claim 1 wherein said current generator comprises means for emitting said second current as a square wave.

8. An apparatus as claimed in claim 1 wherein said electrode system comprises at least one first nerve electrode for the parasympathetic nervous system and at least one second nerve electrode for the sympathetic nervous system.

9. An apparatus as claimed in claim 8 wherein said first nerve electrode comprises a first sub-electrode connectable distally relative to the heart and a second sub-electrode connectable proximally with respect to said heart, at a distance from said first sub-electrode.

10. An apparatus as claimed in claim 9 wherein said current generator comprises a nerve stimulator having a positive output and a negative output from which said first, pulsed current is emitted, and wherein said first sub-electrode is connected to said positive output and said second sub-electrode is connected to said negative output.

11. An apparatus as claimed in claim 8 wherein said second nerve electrode comprises a first sub-electrode connectable distally relative to said heart and a second sub-electrode connectable proximally with said heart, at a distance from said first sub-electrode.

12. An apparatus as claimed in claim 11 wherein said current generator includes a nerve stimulator having a positive output and a negative output, and wherein said first sub-electrode is connected to said negative output of said second nerve stimulator and wherein said second sub-electrode is connected to said positive output.

13. An appartus as claimed in claim 12 wherein said second nerve stimulator comprises a direct current source having said positive and negative.

14. An apparatus as claimed in claim 1 further comprising means for generating pacing pulses and means for generating and delivering defibrillation/cardioversion pulses, and wherein said control means comprises means for controlling said current generator, said means for generating pacing pulses and said means for generating defibrillation/cardioversion pulses, in combination, for delivering a combination of said pacing pulses and said defibrillation/cardioversion pulses to said subject matched to terminate the tachyarrhythmia detected by said tachyarrhythmia detector.

15. A method for providing therapy to the heart of a subject, comprising the steps of:

detecting tachyarrhythmia of said heart; and upon detection of tachyarrhythmia, delivering a first, pulsed current in vivo to the parasympathetic nervous system of said subject in order to activate said parasympathetic nervous system and delivering a second current in vivo to the sympathetic nervous system of said subject for blocking said sympathetic nervous system.

16. A method as claimed in claim 15 wherein the step of delivering said first, pulsed current comprises delivering pulses each having a pulse width in a range of 0.1–1.0 ms in a sequence with a pulse interval in a range from 20–50 ms.

17. A method as claimed in claim 16 wherein the steps of delivering said first, pulsed current comprises delivering said pulses with a pulses width of 0.5 ms.

18. A method as claimed in claim 16 wherein the step of delivering said second current comprises delivering said second current, with a polarity opposite to said first, pulsed current in the form of pulses each having a pulse width in a range from 0.1–1.0 ms in a sequence with a pulse interval in a range from 2–5 ms.

19. A method as claimed in claim 18 wherein the step of delivering said second current comprises delivering said pulses with a pulse width of 0.5 ms.

20. A method as claimed in claim 15 wherein the step of delivering second current comprises delivering said second current as direct current.

21. A method as claimed in claim 15 wherein the step of delivering said second current comprises delivering said second current as a square wave.

22. A method as claimed in claim 13 comprising the additional steps of implanting a first sub-electrode in said subject in contact with said parasympathetic nervous system distally relative to the heart and implanting a second sub-electrode in said subject in contact with said parasympathetic nervous system proximally with respect to said heart, at a distance from said first sub-electrode and wherein the step of delivering said first, pulsed current comprises delivering said first, pulsed current via said first and second sub-electrodes.

23. A method as claimed in claim 22 comprising the additional steps of implanting a nerve stimulator in said subject having a positive output and a negative output from which said first, pulsed current is emitted, connecting said first sub-electrode to said positive output and connecting said second sub-electrode to said negative output.

24. A method as claimed in claim 15 comprising the additional steps of implanting a first sub-electrode in said subject in contact with said sympathetic nervous system distally relative to the heart and implanting a second sub-electrode in said subject in contact with said sympathetic nervous system proximally with respect to said heart, at a distance from said first sub-electrode, and wherein the step of delivering said second current comprises delivering said second current via said first and second sub-electrodes.

25. A method as claimed in claim 24 comprising the additional steps of implanting a nerve stimulator in said subject having a positive output and a negative output, connecting said first sub-electrode to said negative output of said second nerve stimulator, and connecting said second sub-electrode to said positive output of said second nerve stimulator.

26. A method as claimed in claim 25 wherein the step of implanting said second nerve stimulator comprises implanting a direct current source having said positive and negative outputs as said second nerve stimulator.

27. A method as claimed in claim 15 comprising the additional steps of generating pacing pulses and generating defibrillation/cardioversion pulses, and controlling the delivery of said first, pulsed current, delivery of said second current, generation of said pacing pulses and for generation of said defibrillation/cardioversion pulses, in combination, for delivering electrical therapy to said subject matched to terminate the detected tachyarrythmia.

* * * * *